United States Patent [19]

Roy

[11] 4,406,022

[45] Sep. 27, 1983

[54] PROSTHETIC VALVE MEANS FOR CARDIOVASCULAR SURGERY

[75] Inventor: Henry R. Roy, Torrington, Conn.

[73] Assignee: Kathryn Roy, Torrington, Conn.

[21] Appl. No.: 321,988

[22] Filed: Nov. 16, 1981

[51] Int. Cl.³ ............................................... A61F 1/22
[52] U.S. Cl. .......................................... 3/1.5; 137/512;
137/512.1; 137/527; 29/522 R
[58] Field of Search ................... 3/1.5; 137/512.1, 512, 137/527, 527.8

[56] References Cited

U.S. PATENT DOCUMENTS

| | | | |
|---|---|---|---|
| 4,114,202 | 9/1978 | Roy et al. | 3/1.5 |
| 4,272,854 | 6/1981 | Bokros | 3/1.5 |
| 4,276,658 | 7/1981 | Hanson et al. | 3/1.5 |
| 4,306,319 | 12/1981 | Kaster | 3/1.5 |
| 4,326,304 | 4/1982 | Klawitter | 3/1.5 |
| 4,328,592 | 5/1982 | Klawitter | 3/1.5 |
| 4,357,715 | 11/1982 | Klawitter | 3/1.5 |

Primary Examiner—Ronald L. Frinks
Attorney, Agent, or Firm—Hamilton, Brook, Smith & Reynolds

[57] ABSTRACT

Prosthetic valve means for use in heart surgery includes a retainer ring member designed to be attached to portions of a living heart. Leaflet means are supported for hinging movement in the retainer ring to simulate the movement of heart flaps in a human heart. The retainer ring means has inner peripheral wall portions removed to form spaced apart apertures in which occur hinging sockets for receiving hinging stud portions of the leaflet means. The spaced apart apertures are further characterized by upper and lower stop edges against which the leaflets may seat in an alternating manner and the stud portions are freely supported in respective sockets to provide for floating a leaflet in the paths of travel of a flow of blood during the systolic and diastolic functioning of a human heart.

3 Claims, 21 Drawing Figures

PROSTHETIC VALVE MEANS FOR CARDIOVASCULAR SURGERY

BACKGROUND OF THE INVENTION

In the art various forms of prosthetic heart valve means have been devised, in substantially all of which a leaflet structure is employed and supported in hinging relation to a retainer ring to simulate opening and closing of heart flaps as may occur in an aortic valve; or in a one or two valve flap type mitral valve. All of these prior art structures have limitations of one type or another as has been disclosed in more detail in U.S. Pat. No. 4,114,202 issued to the applicant herein in 1978. Included in these limitations are questions regarding durability, efficiency, undesirable blood changes, and the like. These conditions continue to exist and there is a need for an improved hinging leaflet construction which will meet all of the stringent requirements imposed in cardiovascular surgery.

SUMMARY OF THE INVENTION

This invention relates to prosthestic valve means and more particularly to an improved leaflet hinging arrangement by means of which opposite sides of a leaflet element may be freely received in sockets so as to provide for "floating" a leaflet in the path of travel of blood during the systolic and diastolic functioning of a human heart.

It is a cheif object of the invention to provide an improved prosthetic valve construction for heart surgery.

Another object is to devise a retainer ring construction and valve leaflet means in the retainer ring by means of which the leaflet may be delicately balanced so as to be highly responsive to varying blood pressure, as well as offering a minimum amount of resistance to blood pressures and maximized durability.

Another object is to provide a method of forming an expansible leaflet body.

Still another object is to construct tooling which may be employed in forming expansible leaflet means and which may be employed to expand the leaflet means in a manner suitable for installing the hinging studs in a retaining ring member.

The foregoing objectives have been achieved by combining a uniquely constructed retainer ring with expansible leaflet means. Inner wall portions of the retainer ring are recessed to provide hinging apertures which are defined by seating edges angularly disposed to one another. At points closely adjacent to points of intersection of the seating edges are formed hinging sockets. The expansible leaflet means is constructed with hinging studs which are freely supported in respective sockets.

DETAILED DESCRIPTION OF THE INVENTION

Referring in more detail to the drawings, the prosthetic valve means illustrated in general comprises a retainer ring and leaflet means supported in the retainer ring for hinging movement to simulate the movement of valve flaps in a human heart.

Figure 12:
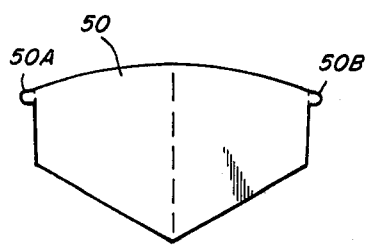
FIG. 12 is a bottom plan view of a preformed leaftlet showing a line of bending.
Figure 13:
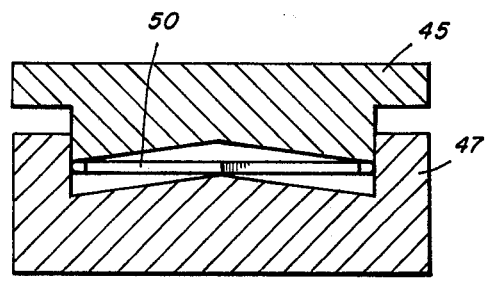
FIG. 13 is a detail cross-sectional view of male and female die members in separated relationship and further showing a leaflet therebetween.
Figure 14:
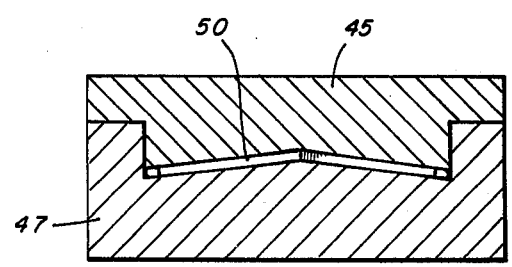
FIG. 14 is a cross-sectional view similar to FIG. 13 with the die members in a closed position and the leaflet of FIG. 13 pressed along the line of bending shown in FIG. 12.
Figure 15:
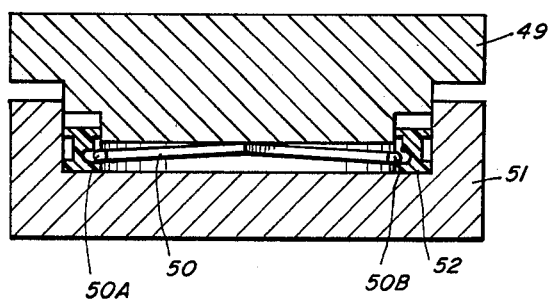
FIG. 15 is a cross-section of die members of FIGS. 13 and 14 and the formed leaflet means is located inside a retaining ring.
Figure 16:
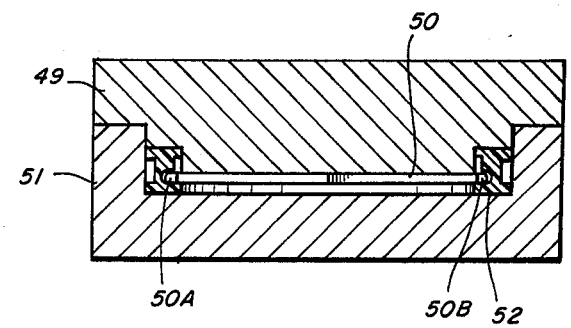
FIG. 16 is a view similar to FIG. 15 with the leaflet means expanded along its medial line of bending, as shown in FIG. 12, to engage hinging studs in the hinging sockets in the retainer ring.
Figure 17:
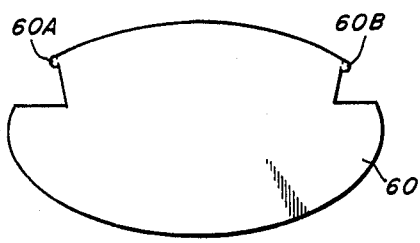
FIG. 17 illustrates a leaflet for use in a mitral type valve.
Figure 19:
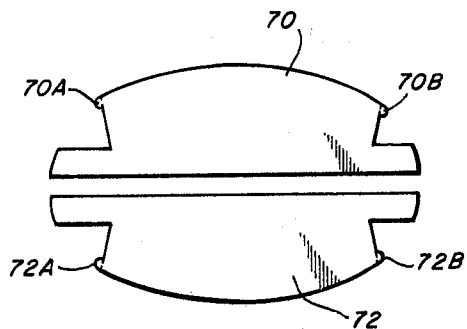
FIG. 19 is an elevational view of leaflet means for use with a mitral type valve.
Figure 18:
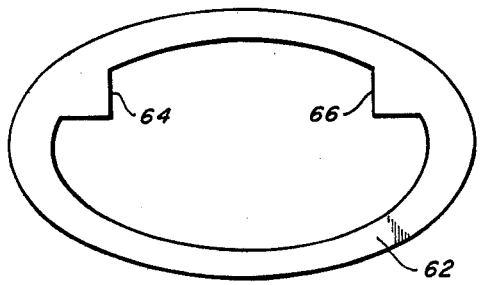
FIG. 18 is a plan view of a retainer ring.
Figure 20:
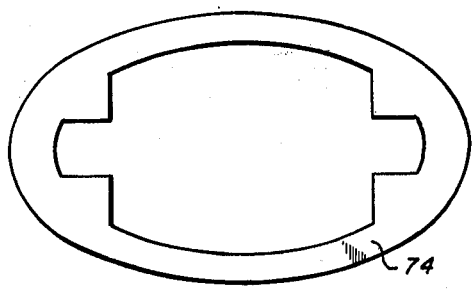
FIG. 20 is a plan view illustrating another retaining ring arrangement.

The retainer ring and leaflet means of the invention may be employed in several types of valve structures. For example, FIGS. 1-12 illustrate a retainer ring and leaflet means arranged to constitute the valve structure of the aortic valve type. FIGS. 13 and 14 illustrate die means employed in forming a leaflet for use in an aortic type valve. FIGS. 15 and 16 illustrate die means for locating and engaging a leaflet in a retainer ring. FIG. 17 is a plan view of a leaflet for use in a mitral type valve. FIG. 18 is a detail view of a retainer ring for receiving the mitral leaflet of FIG. 17. FIG. 19 is a plan view illustrating dual leaflets for a mitral type valve. FIG. 20 is a detail view of a retainer for the leaflets of FIG. 19.

Considering first the aortic valve means of FIGS. 1-12, arrow 2 generally denotes the valve means of the invention and included therein is a retainer ring 4 which is formed around its outer periphery with a channel 6 for receiving an annular suturing body of the class well known in the art. The suturing body is usually made of a textile or plastic material and is used to receive thread or other suturing material to secure the retainer ring in place in a human heart.

At its inner periphery retainer ring 4 is formed with arcuate surfaces as 8, 10 and 12 which are spaced apart by inwardly converging lobes as 14, 16, and 18. The lobes 14, 16 and 18 present intersecting walls 14A and 14B, 16A and 16B, and 18A and 18B, respectively.

By means of the lobular construction disclosed there are defined spaces in which three leaflets as 20, 22 and 24 may be received for hinging movement. As is better shown in FIG. 3, each of the leaflets 20, 22 and 24 are constructed of a similar flat configuration of metal or other material and in FIG. 5 leaflet 20 is shown removed from the retainer ring. As will be more clearly understood from an inspection of FIG. 5, leaflet 20 is formed with an arcuate edge 20A which is substantially complementary to the arc of curvature of ring part 8.

Extending inwardly a short distance from the arcuate edge 20A are seating edges 20B and 20C which occur in substantially parallel relationship and which are further formed with hinging stud portions as 20D and 20E. Coextensive with the edges 20B and 20C are converging edges 20F and 20G which meet at an angle of approximately 60° and with the three leaflets 20, 22 and 24 in nearly abutting relationship, as shown in FIGS. 1 and 2, they substantially close the central opening of the retainer ring.

It should be understood that the leaflet 22 is similarly constructed with seating edges and hinging stud portions and is supported for hinging movement between lobes 16 and 18. Likewise, the leaflet 24 is constructed with seating edges and hinging stud portions and is supported for hinging movement between the lobes 14 and 18.

Figure 5:
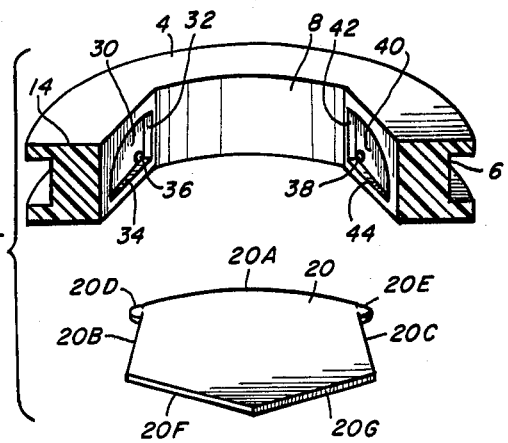
FIG. 5 is a fragmentary perspective view of a valve retainer ring with a leaflet removed therefrom.

In accordance with the invention, the leaflet member 20 has its seating edges received in hinging apertures 30 and 40. As shown in FIG. 5, the hinging aperture 30 is defined by angularly extending stop edges 32 and 34 which in one preferred form meet at right angles. At a point near the intersection of the stop edges 32 and 34 the inner surface of aperture 30 is recessed to provide a socket 36 which may, for example, be of a ball shaped configuration and which is of a size slightly greater than the size of the hinging stud 20D (FIG. 5) so that the hinging stud 20D may be loosely received therein, and no other part of the leaflet is allowed to come into contact with the retaining ring.

Figure 1:
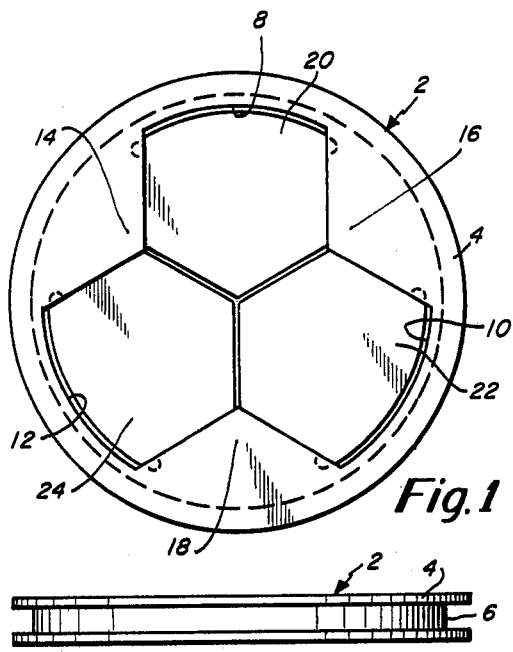
FIG. 1 is a plan view of an aortic valve structure of the invention.
Figure 3:
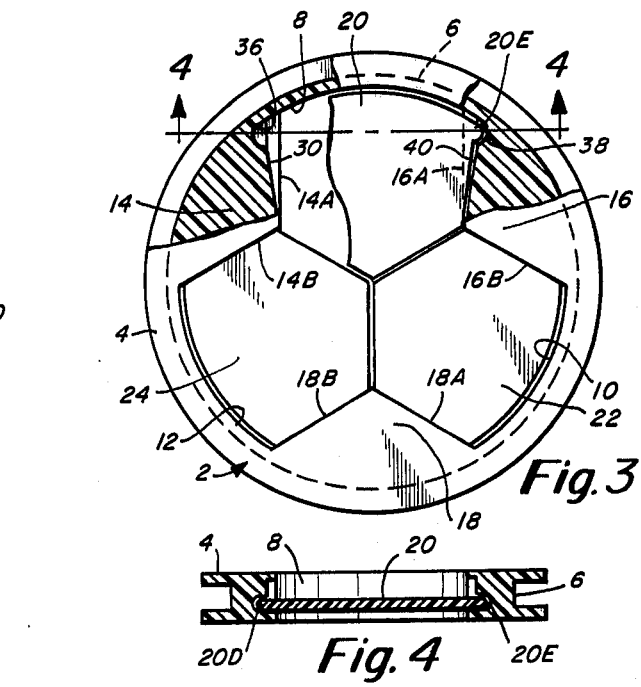
FIG. 3 is a plan view of the valve of FIGS. 1 and 2 with portions of a ring structure shown in cross section and a leaflet member partly broken away.
Figure 2:
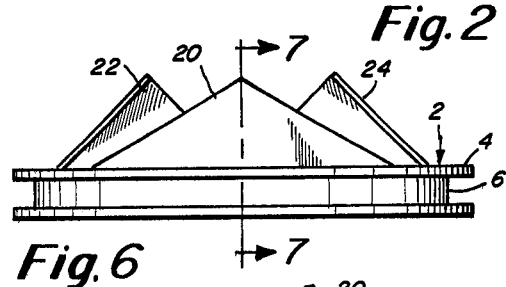
FIG. 2 is a side elevational view of the structure of FIG. 1.
Figure 4:
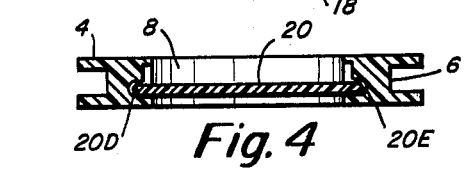
FIG. 4 is a cross-section taken on the line 4—4 of FIG. 3.
Figure 6:
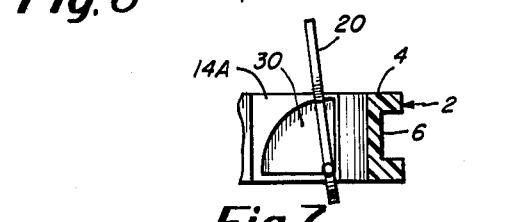
FIG. 6 is a side elevational view of the valve and ring of FIG. 1, but showing the leaflets in an open position.

In a closed position of the leaflet 20, as shown in FIG. 1, the edge 20B seats against the stop edge 34. When swung into an open position, as shown in FIG. 6, the leaflet has its edge 20B seated against the stop edge 32. Similarly, the hinging stud 20E of leaflet 22 is loosely received in a socket 38 formed in an inner wall of an aperture 40 defined by stop edges 42 and 44, as shown in FIG. 5 against which edge 20C may seat periodically.

Figure 7:
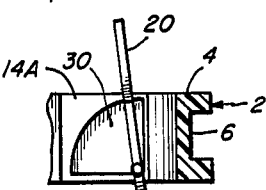
FIG. 7 is a cross section taken on the line 7—7 of FIG. 6.
Figure 8:
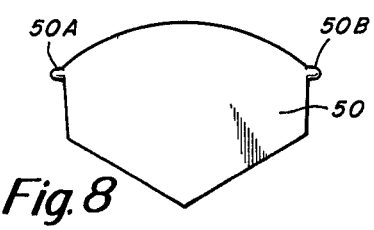
FIG. 8 is a plan detail view of a leaflet as viewed from an upper side thereof.
Figure 9:
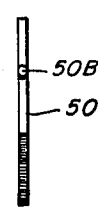
FIG. 9 is a side elevational view of the leaflet of FIG. 8.

With the arrangement of components disclosed and illustrated in FIG. 7 there is realized a unique supporting of the leaflets so that they are in effect floating in the path of flow of blood pumped by a heart during systolic and diastolic functioning and a delicate balancing is achieved which is highly important in responding to heart pressures with little, if any, resistance or wear problems arising.

An important feature of the invention resides in a novel method and apparatus for forming the leaflets and installing them in respective sockets in freely disposed relationship with only the seating edges and the hinging stud portions contacting the retainer ring so as to provide for floating of the leaflets in a flow of blood. The novel method is characterized by first forming a leaflet of a suitable shape as an expansible element as shown in FIG. 12, having a line of bending indicated in dotted lines and extending medially of the leaflet 50. Thereafter, the expansible leaflet is installed with its hinging stud portions being expanded sufficiently so that the studs are inserted in respective sockets in a freely disposed relationship.

Figure 10:
FIG. 10 is another detail view of the leaflet of FIGS. 8 and 9 after having undergone a forming operation.
Figure 10A:
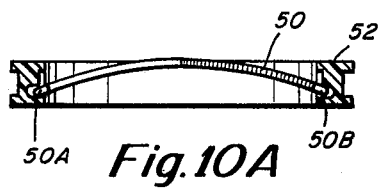
FIG. 10A illustrates the formed leaflet of FIG. 10 in a position to be inserted in a retainer ring member.
Figure 11:
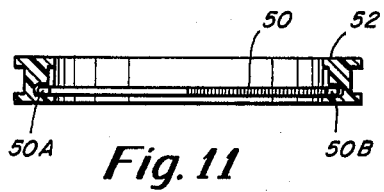
FIG. 11 is a cross sectional view of a retainer ring member with a leaftlet fully engaged therein.

In FIG. 13 there is illustrated a male die 45 and a female die 47 in which a leaftlet component as 50 (FIG. 10A) is first positioned and thereafter the leaflet (as shown in FIG. 14) is pressed into an expansible configuration having a line of bending extending medially of the leaflet such as, for example, that shown in FIGS. 10 and 12.

In FIG. 15 there is illustrated die members 49 and 51 and the pressed component 50 is shown located in a retainer ring 52. FIG. 16 illustrates the die members in a closed position with expansible leaftlet 50 being expanded with its hinging studs 50A and 50B engaged in respective sockets of the ring 2 in freely disposed but firmly captured relationship with only the hinging studs and seating edges making contact with the retaining ring.

In FIG. 17 there is illustrated a single leaflet 60 for use in a mitral type valve. The leaflet 60 is formed with hinging studs as 60A, 60B which are constructed in the manner already described.

In FIG. 18 there is shown a retainer ring 62 having sides 64 and 66 which are formed with sockets similar to those earlier described. It will be understood that leaftlet 60 may be installed by die means similar to those disclosed above.

In FIG. 19 there are shown dual leaflet elements 70 and 72 for use in forming another form of mitral valve.

FIG. 20 illustrates a retainer ring 74 in which hinging studs as 70A, 70B, 72A and 72B may be engaged for hinging movement.

I claim:

1. Improved prosthetic valve means for use in cardiovascular surgery including a retainer ring and leaflet members supported in the retainer ring for hinging movement to simulate movement of heart flap members in opening and closing a passageway through the retainer ring for flow of blood,
characterized in that each of the leaflet members includes an arcuate portion occurring in spaced relation to adjacent portions of the retainer ring, hinging studs located at opposite extremities of each of the arcuate portions, seating edges extending inwardly from respective hinging studs in substantially parallel relationship and inner extremities of the leaflet members formed with converging edges which intersect respective seating edges of the leaflets, and said valve means further characterized in that the inner peripheral surface of the retainer ring is constructed with circumferentially spaced apart lobes, each of which has inwardly projecting sides which intersect one another, and each of the lobe sides being recessed to form a hinging aperture defined by vertically and horizontally disposed stop edges which intersect one another substantially at right angles, said stop edges being constructed and arranged to receive the said seating edges thereagainst, each of the hinging apertures being formed at points closely adjacent to points of intersection of the stop edges with hinging stud sockets and each of the said leaflets being formed with medial lines of bending along which the leaflets are expanded to locate the said hinging studs in respective hinging stud sockets and to provide for only hinging studs and seating edges being engageable with the retainer ring.

2. The invention of claim 1 in which the leaflet seating edges are seated against respective horizontally disposed stop edges at a closed position of the valve and the seating edges seated against the vertically disposed stop edges when the valve is moved into an opened position.

3. The invention of claim 1 in which the hinging stud sockets are of a size slightly larger than the size of the hinging studs to loosely confine the studs and to provide for floating the leaflets in the paths of travel of flows of blood during the cystolic and diastolic functioning of the human heart.

* * * * *

UNITED STATES PATENT AND TRADEMARK OFFICE
CERTIFICATE OF CORRECTION

PATENT NO. : 4,406,022

DATED : September 27, 1983

INVENTOR(S) : Henry R. Roy, Kathryn Roy

It is certified that error appears in the above—identified patent and that said Letters Patent is hereby corrected as shown below:

On the title page:

The names of the inventors listed on the front of the patent are incorrect.

The name "Henry R. Roy" should be changed to read ---Henry A. Roy---.

The name "Kathryn Roy" should be changed to read ---Katherine Roy---.

Signed and Sealed this

Nineteenth Day of March 1985

[SEAL]

Attest:

DONALD J. QUIGG

Attesting Officer  Acting Commissioner of Patents and Trademarks